United States Patent [19]
Inakagata et al.

[11] Patent Number: 5,493,747
[45] Date of Patent: Feb. 27, 1996

[54] ELECTRIC TOOTHBRUSH

[75] Inventors: Satoru Inakagata, Hirakata; Yoji Kawamoto, Hikone, both of Japan

[73] Assignee: Matsushita Electric Works, Ltd., Osaka, Japan

[21] Appl. No.: 280,766

[22] Filed: Jul. 25, 1994

[30] Foreign Application Priority Data

Jul. 27, 1993 [JP] Japan ...................... 5-185273

[51] Int. Cl.⁶ .......................... A61C 17/34; A46B 13/02
[52] U.S. Cl. ................................................ 15/22.1
[58] Field of Search ...................... 15/22.1, 22.2, 15/22.4, 23, 24

[56] References Cited

U.S. PATENT DOCUMENTS 4,698,869  10/1987  Mierau et al. ..................... 15/22.1

FOREIGN PATENT DOCUMENTS 4012413  10/1991  Germany ................................. 15/22.1
2002159   2/1992  WIPO ..................................... 15/22.1

*Primary Examiner*—Edward L. Roberts, Jr.
*Attorney, Agent, or Firm*—Stevens, Davis, Miller & Mosher

[57] ABSTRACT

An electric toothbrush with a control circuit capable of stopping the brushing operation when the brush is pressed against an user's teeth with an excessive force. The electric toothbrush comprises a housing which carries a shaft mounting a brush. The housing incorporates a rotary electric motor and a motion conversion mechanism which converts a rotational movement of the motor to a reciprocatory movement of the shaft for reciprocating said brush. A pressure sensor is provided to sense a brush pressure being applied back to the brush as a counter-action when pressing the brush against the user's teeth and to produce a stop signal when the sensed brush pressure exceeds a predetermined limit level.

23 Claims, 10 Drawing Sheets

FIG. 4
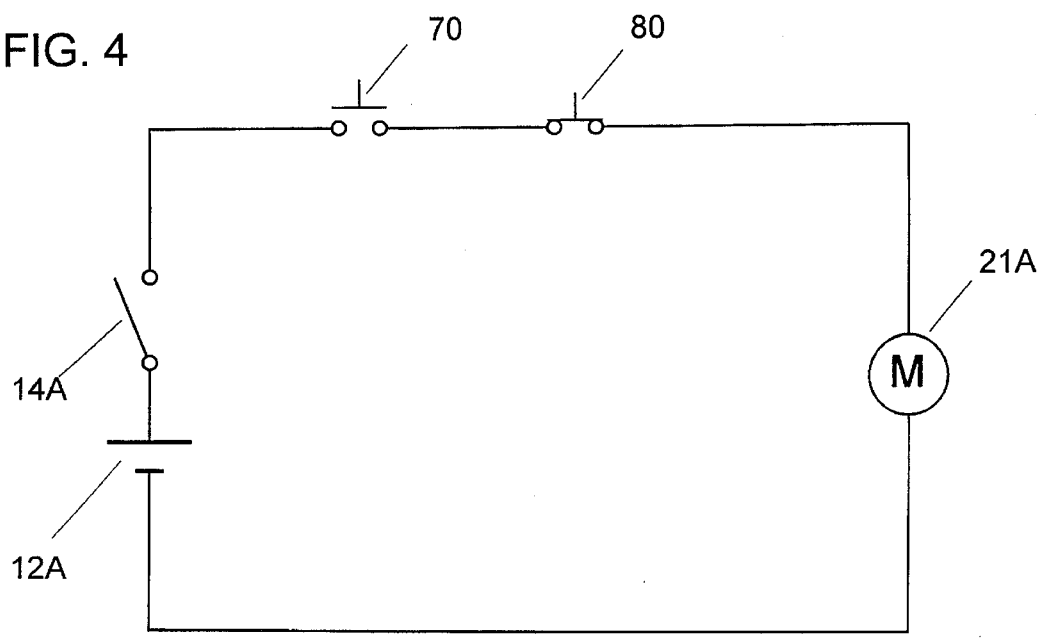
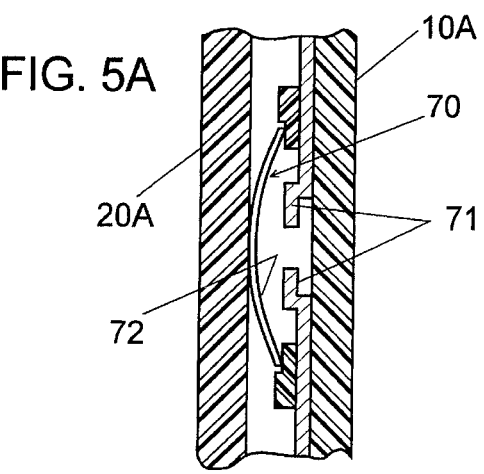
FIG. 5A
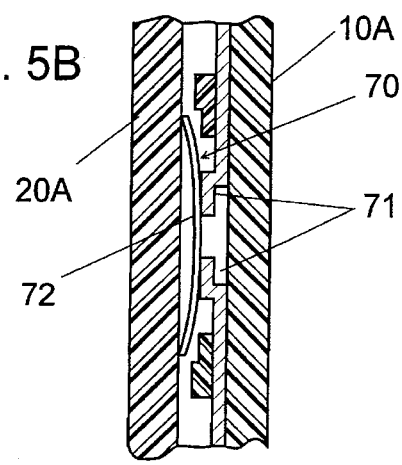
FIG. 5B
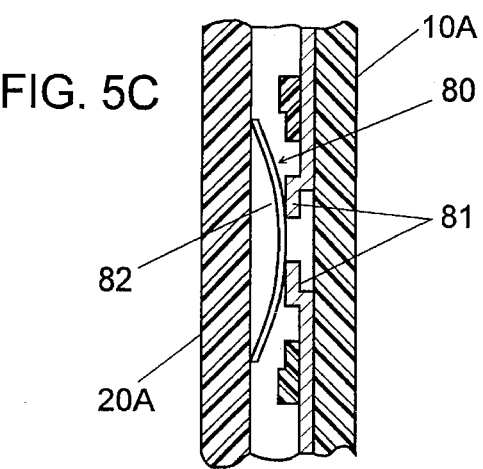
FIG. 5C
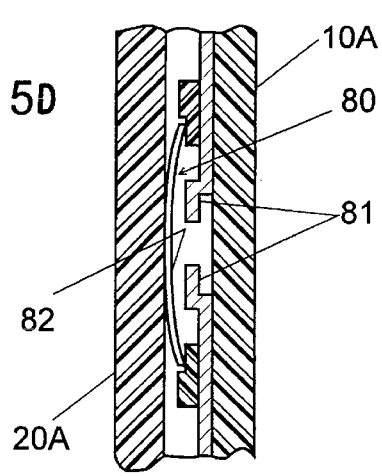
FIG. 5D Vw trigger pulse output of multivibrator 114 smoothd voltage fed to comparator 65C

ELECTRIC TOOTHBRUSH

BACKGROUND OF THE INVENTION

1. Field of the Invention

The present invention is directed to an electric toothbrush, and more particularly to an electric toothbrush with a control circuit capable of stopping brushing operation when pressed forcibly against teeth of an user.

2. Description of the Prior Art

Electric toothbrushes have been widely utilized in the art. One typical example is disclosed in the Japanese Patent Early Publication (KOKAI) No. 61-22812. This prior art toothbrush includes a pressure sensor which monitors a brush pressure applied to teeth of an user during tooth brushing, and includes a display or speaker to inform the user of the monitored brush pressure for assisting the user to perform the tooth brushing at an optimum pressure. However, the user is still required to take care of pressure control and therefore might hurt one's teeth and/or gums when pressing the brush at an excessive pressure accidentally or unintentionally. In this sense, great care should be exercised on the user when using the electric toothbrush.

SUMMARY OF THE INVENTION

The above problem has been eliminated in the present invention which provides an improved electric toothbrush with a control circuit capable of stopping the brushing operation when the brush is pressed with excessive pressure against the teeth of the user. The electric toothbrush in accordance with the present invention comprises a housing which carries a shaft mounting a brush. The housing incorporates a rotary electric motor and a motion conversion mechanism which converts a rotational movement of the motor to a reciprocatory movement of the shaft for reciprocating said brush. A pressure sensor is provided to sense a brush pressure being applied back to the brush as a counter-action when pressing the brush against the user's teeth and to produce a stop signal when the sensed brush pressure exceeds a predetermined limit level. Also included is a control circuit which is connected to stop the motor in response to the stop signal.

Accordingly, it is a primary object of the present invention to provide an electric toothbrush which is capable of stopping the motor when the brush pressure increases excessively for safe protection of the teeth and gums.

The electric toothbrush is preferred to include a selector which give the limit level from a plurality of set values so that the toothbrush can be easily suited to requirements by different users of different limit levels.

It is therefore another object of the present invention to provide an electric toothbrush which assures the user the possibility to select one's own limit level for optimum tooth brushing.

In a preferred embodiment, the control circuit includes a constant speed regulator for rotating the motor at a constant speed irrespective of variations in the brush pressure so long as the brush pressure is below the limit level. The constant speed is selected from a plurality of set values so that the user can enjoy tooth brushing at one's favorite rotation speed of the motor, i.e. reciprocation speed of the brush.

Alternately, the control circuit may include a proportional regulator for increasing the rotation speed of the motor in proportion to the increasing brush pressure so long as the brush pressure is below the limit level. This control is most effective for rapid tooth brushing at an increased pressure and increased rotation speed of the motor, i.e., reciprocation speed of the brush.

The control circuit includes a starter which starts the motor only after the brush pressure increases up to a predetermined start level lower than the limit level so that the motor rotates to effect tooth brushing only within the pressure range between the start level and the limit level. Therefore, the motor is free from unnecessary idling and can be activated only after the brush is pressed against the teeth at a suitable pressure. In other words, when the brush is released from the user's teeth, the motor is inactivated unless it is again pressed against the teeth.

Preferably, the pressure sensor is in the form of a current sensor which monitors a motor current and which produces the stop signal when the motor current exceeds a predetermined level corresponding to the limit level. Since the motor current is well representative of the brush pressures which is resultant of components applied back to the brush in all directions with respect to the tip face of the brush, a more consistent control is possible to stop the motor in order to avoid hurting the teeth and gums. In this connection, the control circuit may additionally include a calibrator which obtains an initial current level measured when the motor rotates under substantially a no load condition or an idling condition. The calibrator weights the initial current level upon a predetermined set level to determine the limit level which is consistently free from being influenced by environmental factors such as temperature, humidity, or the kind of the brush used which may vary the motor current itself. Thus, it is possible to determine the limit level which is solely indicative of a dangerous pressure level which hurts the teeth and gums.

These and still other objects and advantageous features of the present invention will become more apparent from the following detailed description of the preferred embodiments when taken in conjunction with the attached drawings.

BRIEF DESCRIPTION OF THE DRAWINGS

FIG. 4 is a circuit diagram of an electric toothbrush in accordance with a second embodiment of the present invention;

FIGS. 5A to 5D are sectional views of pressure sensors utilized in the circuit of FIG. 4, respectively with different switching conditions;

DETAILED DESCRIPTION OF THE EMBODIMENTS

Figure 1:
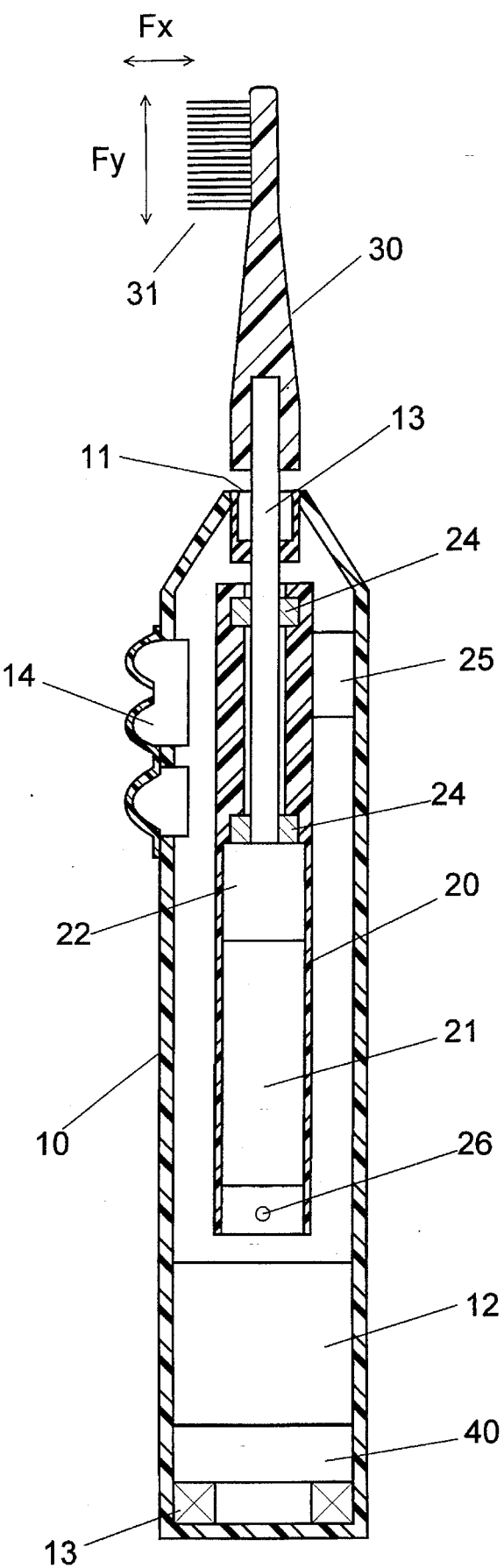
FIG. 1 is a vertical section of an electric toothbrush in accordance with a first embodiment of the present invention.
Figure 2:
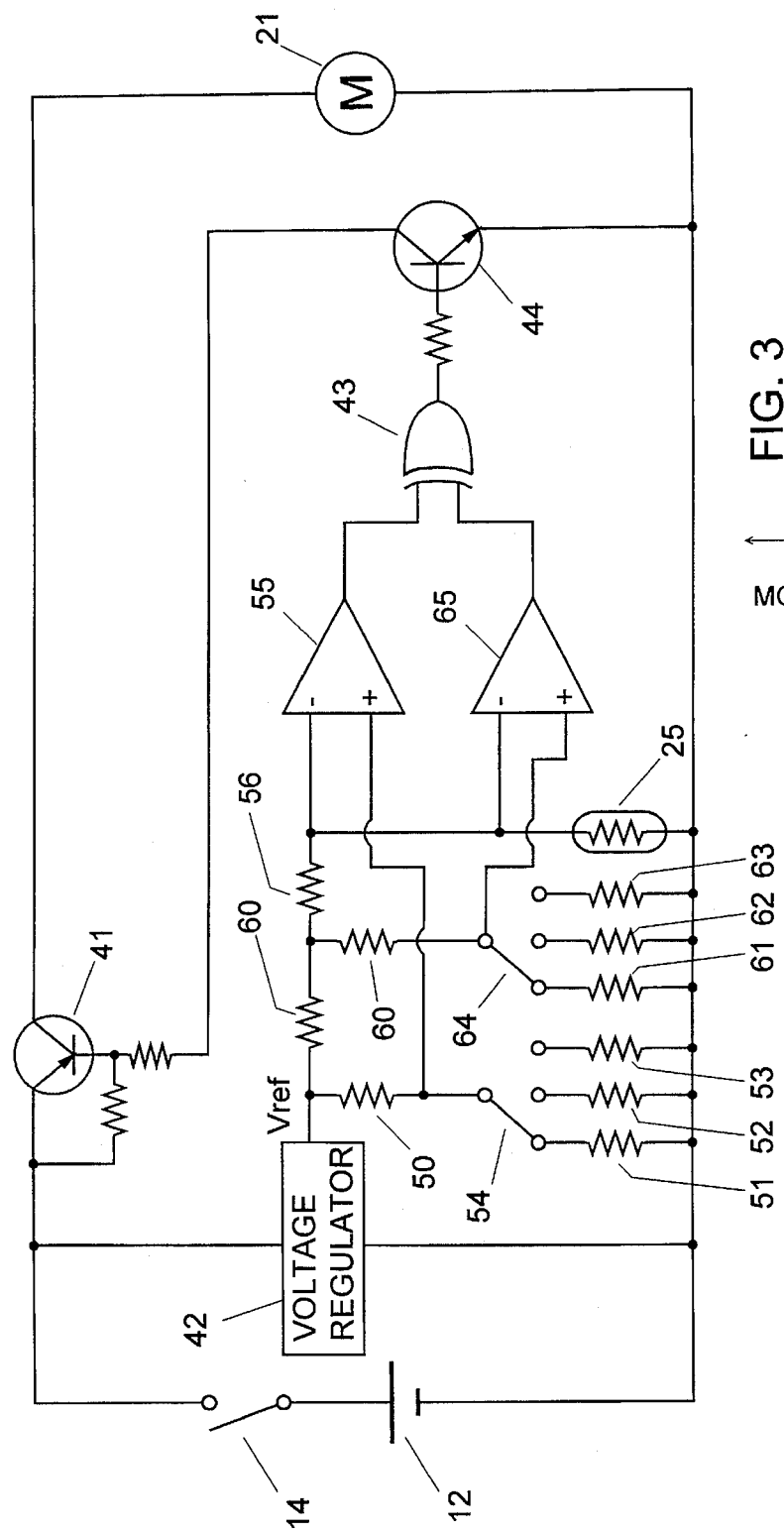
FIG. 2 is a circuit diagram of the electric toothbrush.
Figure 3:
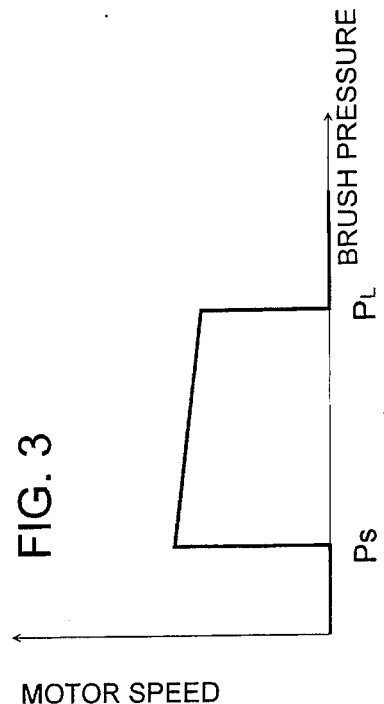
FIG. 3 is a graph illustrating the operation of the toothbrush.

First Embodiment <FIGS. 1 to 3>

Referring now to FIG. 1, there is shown an electric toothbrush in accordance with a first embodiment of the present invention. The electric toothbrush comprises a generally cylindrical housing 10 grasped by a hand of a user and a detachable stem 30 formed at its top end with a brush 31. The housing 10 incorporates a holder 20 carrying an electric DC motor 21, a motion-converter 22 which reduces the motor speed and converts a rotary motion of the motor output into a reciprocatory motion of a shaft 23 for reciprocation of the brush 31 along and/or about a longitudinal axis of the shaft 23. The shaft 23 extends outwardly of the housing 10 through a bushing 11 in a coaxial relation to a longitudinal axis of the housing 10 and is supported to the holder 20 by means of a spaced pair of bearings 24. Also included in the housing 10 are a rechargeable battery 12 energizing the motor 21, a coupling coil 13 for coupling with an external charger to charging the battery 12, and a circuit block 40 composed of electronic components forming a control circuit to control the motor 21. The holder 20 is pivotally supported to the housing 10 at its lower end by means of a pivot pin 26 so that the holder 20 is allowed to pivot together with the stem 30 within the housing 10 in response to the pressure applied back to the shaft 23 as a counter-action when pressing the brush 31 against the teeth of the user. The bushing 11 fitted around the shaft 23 is made of a resilient material to permit the pivotal movement of the holder 20 within a limited extent. A pressure sensor 25 is provided in the housing 10 in such a relation as to be compressed when the holder 20 is displaced as a result of the brush being pressed against the user's teeth. The pressure sensor 25 is a resistive element such as a strain gauge which increases its electrical resistance when compressed to a greater extent and therefore provides a parameter indicative of a brush pressure at which the brush 31 is pressed against the user's teeth. In this sense, the pressure sensor 25 provides an output indicative of the pressure acting in the direction substantially perpendicular to the tip face of the brush 31, as indicated by Fx in FIG. 1. It may be equally possible that the pressure sensor 25 provides an output indicative of the pressure acting in the direction substantially parallel to the tip face of the brush, as indicated by Fy in FIG. 1, by movably supporting the holder 20 along the axis of the shaft 23 and locating the pressure sensor to sense the movement of the holder along that axis. However, the pressure sensor 25 in the illustrated position may give the output indicative of the brush pressure in Fy direction from a vertical component of the angular displacement of the holder 20 about the pivot pin 26. The housing 10 is provided with a power switch 14 for energizing the motor 21 and a selector 15 at which user can select a start level and a limit level for the brush pressure at which the motor 21 starts and stops, respectively, as will be discussed hereinafter.

FIG. 2 illustrates a diagram of the control circuit which comprises a switching element 41 in the form of a bipolar transistor connected in series with the power switch 14 across the battery 12. A voltage regulator 42 is connected in circuit to provide a reference voltage Vref which is processed to determine the start level or voltage at which the motor 21 starts and the limit level or voltage at which the motor 21 stops. The start voltage is selected from three set voltages which are determined respectively by voltage dividers of a common resistor 50 and a first resistor 51, of common resistor 50 and a second resistor 52, and of common resistor 50 and a third resistor 53. The selector 15 comprises a first switch 54 for connecting the common resistor 50 selectively to one of the resistors 51, 52, 53 of different resistivity to give the start voltage of a particular level to an inverted input of a first comparator 55. Likewise, the limit voltage is selected from three set voltages which are determined respectively by voltage dividers of a common resistor 60 and a first resistor 61, of common resistor 60 and a second resistor 62, and of common resistor 50 and a third resistor 63. The selector 15 also has a second switch 64 for connecting the common resistor 60 selectively to one of the resistors 61, 62, 63 of different resistivity to give the limit voltage of a particular level to an inverted input of a second comparator 65. The pressure sensor 25 is connected to a resistor 56 to give a divided voltage of the reference voltage Vref from the voltage regulator 42, as indicating the brush pressure, commonly to inverted inputs of first and second comparators 55 and 65. Outputs of first and second comparators 55 and 65 are fed to an exclusive OR gate 43 which provides a high level output when one of the comparators provides a high level output and otherwise provide a low level output to a drive transistor 44. Transistor 44 is connected to turn on and off the switching element 41 in response to the high and low level output from exclusive OR gate 43, respectively, such that the motor 22 is activated only while the monitored brush pressure is within a range of between the start level and the limit level. That is, when the brush pressure is lower than the start level, i.e., the brush 31 is not yet pressed sufficiently to the user's teeth, the pressure sensor 25 provides to the inverting inputs of first and second comparators 55 and 65 a correspondingly low voltage lower than the start and of course the limit voltages so that both comparators 55 and 65 provide "H" outputs to cause the exclusive OR gate 43 gives "L" output for making the switching element 41 non-conductive, disabling rotation of the motor 21 and therefore reciprocation of the brush 31. When the brush pressure reaches the start level but not exceeding the limit level, i.e., the brush 31 is pressed sufficiently but not so hard, the pressure sensor 25 provides a corresponding voltage which is higher than the start voltage but lower than the limit level, in response to which the first comparator 55 provides "H" output while the second comparator 65 still provides "L" output. Therefore, exclusive OR gate 43 gives "H" output to the driver 44 to thereby turn on the switching element 41 and start rotating the motor 21 for initiating the tooth brushing. Upon the brush pressure exceeding the limit level, the pressure sensor 25 provides a corresponding high voltage to the comparators 55 and 65 so that both comparators provides "H" outputs, causing the exclusive OR gate 43 to provide "L" output for stopping the motor 21. In this manner, tooth brushing at excessive pressure can be successfully avoided to protect the teeth and gums of the user, in addition to eliminating unnecessary idling of the motor prior to tooth brushing. It is noted in this connection, the user can select one' own start level Ps and limit level PL by means of switches 54 and 64 so as to perform the tooth brushing at an optimum range of brush pressure, as shown in FIG. 3. As apparent from the above, the motor 21 can resume rotating when the brush pressure comes back into the range from the starting level to the limit level as well as that the motor 21 stops as the brush pressure reduced below the start level. Although the motor speed is shown in FIG. 3 to abruptly increase and decrease upon reaching the start level Ps and exceeding the limit level PL, respectively, the motor speed actually increases and decreases gradually in consideration of the pressure or load being applied to the motor. Further, the motor speed may be controlled to gradually increase and decrease as necessary. The above embodiment may be modified to eliminate the first comparator 55 with associated components so that the motor starts upon closing the power switch 14 and stops when the brush pressure exceeds the limit level.

Second Embodiment <FIGS. 4, FIGS. 5A to 5D>

FIG. 4 illustrates a circuit diagram of an electric toothbrush in accordance with a second embodiment which has a mechanical structure identical to the first embodiment except that a pair of first and second pressure sensors 70 and 80 with electrical contacts is utilized in combination. Like parts are designated by like numerals with a suffix letter of "A" for easy reference purpose. As shown in FIGS. 5A to 5D, the pressure sensor 70 and 80 are of same configuration which comprises a pair of fixed contacts 71, 81, and a snap-action movable plate 72, 82 which is disposed in opposed relation to fixed contacts 71, 81 and engaged with the holder 20A of the motor 21. First pressure sensor 70 is a normally open switch of which movable plate 72 snaps over to close the fixed contacts 71 when the brush pressure applied back to the holder 20A reaches the start level. While, on the other hand, second pressure sensor 80 is a normally closed switch of which movable plate 82 snaps over to open the fixed contacts 82 when the brush pressure exceeding the limit level. First and second pressure sensors 70 and 80 are inserted in series between the motor 21A and the battery 12A such that the motor 21A is permitted to rotate for reciprocation of the brush only under the condition where the brush pressure is higher than the start level and at the same time lower than the limit level, in much the same way as in the first embodiment.

Figure 6:
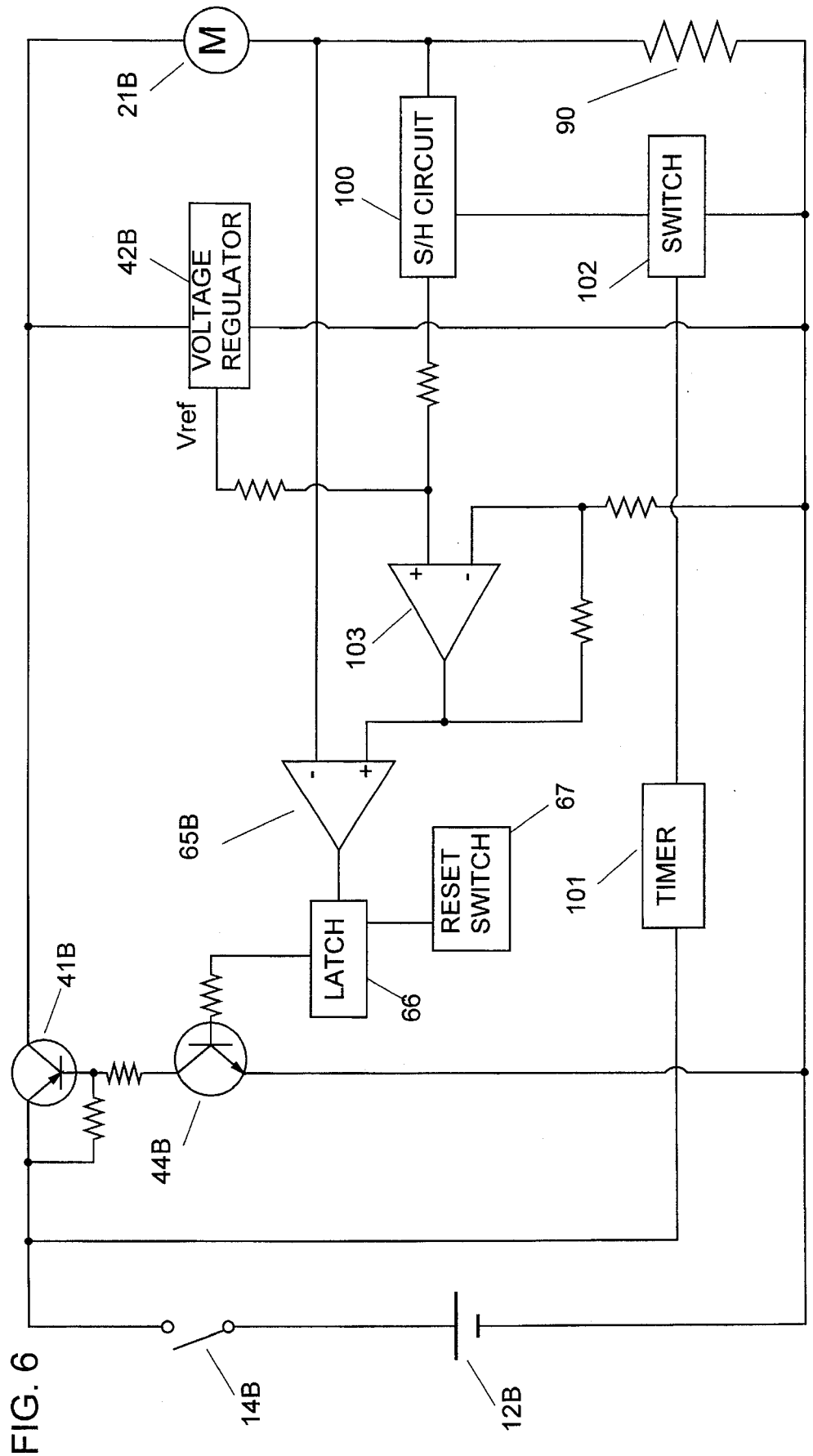
FIG. 6 is a circuit diagram of an electric toothbrush in accordance with a third embodiment of the present invention.

Third Embodiment <FIG. 6>

FIG. 6 illustrates a circuit diagram of an electric toothbrush in accordance with a third embodiment of the present invention which is identical in mechanical structure to the first embodiment except that the brush pressure is measured in terms of a motor current flowing through the DC motor 21B in view of the fact that the motor current is proportional to the load, i.e., the brush pressure in this instance applied to the motor as representing a resultant of pressure components acting in the directions perpendicular and parallel to the tip face of the brush. Like components are designated by like numerals with a suffix letter of "B". A switching transistor 41B is connected in series with the motor 21B to activate and deactivate the motor 21B. A current sensing resistor 90 is inserted in series with motor 21C to give a corresponding voltage to an inverting input of a comparator 65B as indicative of the brush pressure. Comparator 65B receives at its non-inverting input a limit voltage indicative of the limit level at which the motor is intended to stop and also compensating for possible variations of environmental conditions such as temperature, humidity, and the kind of the brush utilized, as will be discussed later. When the motor current is sensed to be below the limit voltage, comparator 65B responds to produce "H" output which makes a transistor 44B conductive and therefore makes switching transistor 41B conductive to keep rotating the motor 21B. Upon the brush pressure exceeds the limit level, comparator 65B provides "L" output which is latched at latch 66 and turn off transistor 44B and transistor 41B for stopping the motor 21B. "L" output of comparator 65B is latched at latch 66 until the circuit is reset, i.e., power switch 14B is turned off and then on. Included in the control circuit is a sample-and-hold circuit 100 which is operated only for a short time period upon closing the power switch 14B to obtain an initial voltage indicative of the motor current caused to flow under substantially no load condition. Thus the obtained voltage is held and fed to an operational amplifier 103 where it is added to a predetermined reference voltage supplied from voltage regulator 42B to give the limit voltage or the limit level as well as accounting for the environmental conditions as stated above. With this result, a more consistent control can be made substantially free from the environmental variations. A timer 101 is provided to activate the sample-and-hold circuit 100 through a switch 102 only for the limited time interval to sample the motor current and thereafter deactivate the sample-and-hold circuit 100. A reset switch 67 is added in the control circuit of FIG. 6 to release the latch 66 so as to enable restarting of the motor 21B when the brush pressure is lowered below the limit level.

Figure 7:
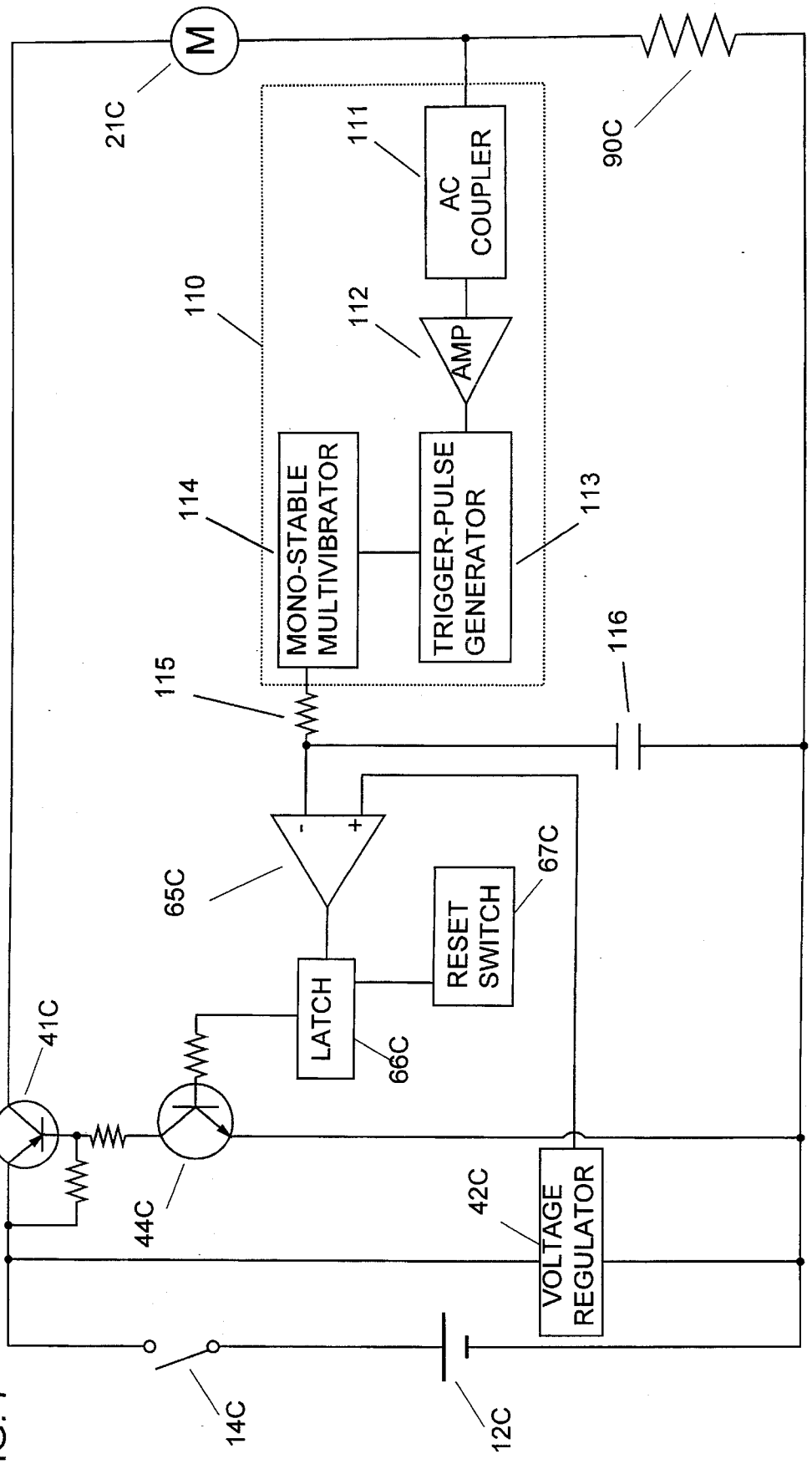
FIG. 7 is circuit diagram of an electric toothbrush in accordance with a fourth embodiment of the present invention.

Fourth Embodiment <FIG. 7>

Figure 8A:
FIGS. 8A to 8D are graphs illustrating the operation of the circuit of FIG. 7.
Figure 8B:
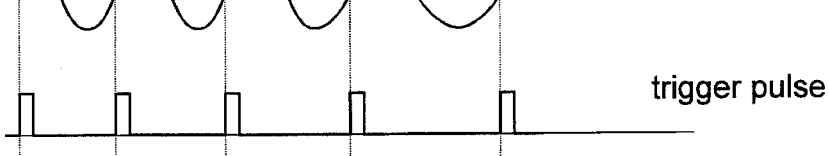
Figure 8C:
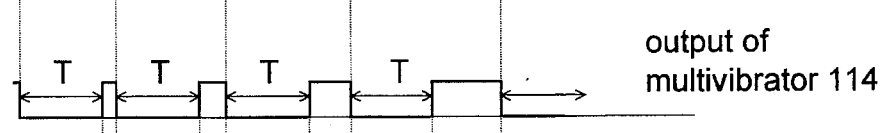
Figure 8D:
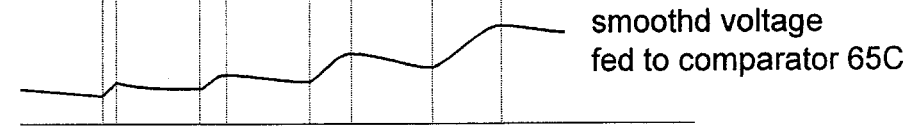

FIG. 7 illustrates a circuit diagram of a control circuit for an electric toothbrush in accordance with a fourth embodiment of the present invention which is similar to the third embodiment of FIG. 6 except for a provision of a waveform analyzer 110 which determines the brush pressure from the waveform of a reverse voltage developed across the resistor 90C connected in series with the motor 21C. The analyzer 110 comprises an AC-coupler 111 which is connected to give a voltage Vw of which the waveform corresponds to a change of the reverse voltage developed across resistor 90C, as shown in FIG. 8A. The resulting voltage Vw is then amplified through an amplifier 112 and fed to a trigger pulse generator 113 which provides a train of trigger pulses, as shown in FIG. 8B, occurring at a zero-cross timing when the reverse voltage goes to positive from negative. The trigger pulses are fed to a mono-stable multivibrator 114 which provides an output of FIG. 8C which has a fixed low level period T from the onset of the trigger pulses. The output of multivibrator 114 is fed to an inverting input of comparator 65C through a smoothing circuit of a resistor 115 and a capacitor 116. FIG. 8D shows the resulting smoothed voltage across capacitor 116. Comparator 65C receives at its non-inverting input a limit voltage from voltage regulator 42C indicative of the limit voltage. As the bush pressure increases, the motor speed decreases correspondingly to thereby shorten the cycle of voltage Vw of FIG. 8A. Thus, the output of the multivibrator 114 gives the output of an increasing duty ratio, which in turn increases the smoothed voltage across capacitor 116, as shown in FIG. 8D, which is indicative of the brush pressure. When the smoothed voltage further increases beyond the limit voltage fed from voltage regulator 42C, comparator 65C responds to produce "L" output which is latched at latch 66C and turn off transistor 44C and then transistor 41C, thereby stops feeding motor current to stop motor 21C. "L" output from comparator 65C is kept latched until the power switch 14C is turned off and again turned on. When the smoothed voltage of capacitor 116 is below the limit voltage, i.e., the brush pressure is below the limit level, comparator 65C provides "H" output to turn on transistors 44C and 41C, to keep rotating the motor 21C. A reset switch 67C is added in the control circuit of FIG. 7 to release the latch 66C so as to enable restarting of the motor 21C when the brush pressure is lowered below the limit level.

Figure 9:
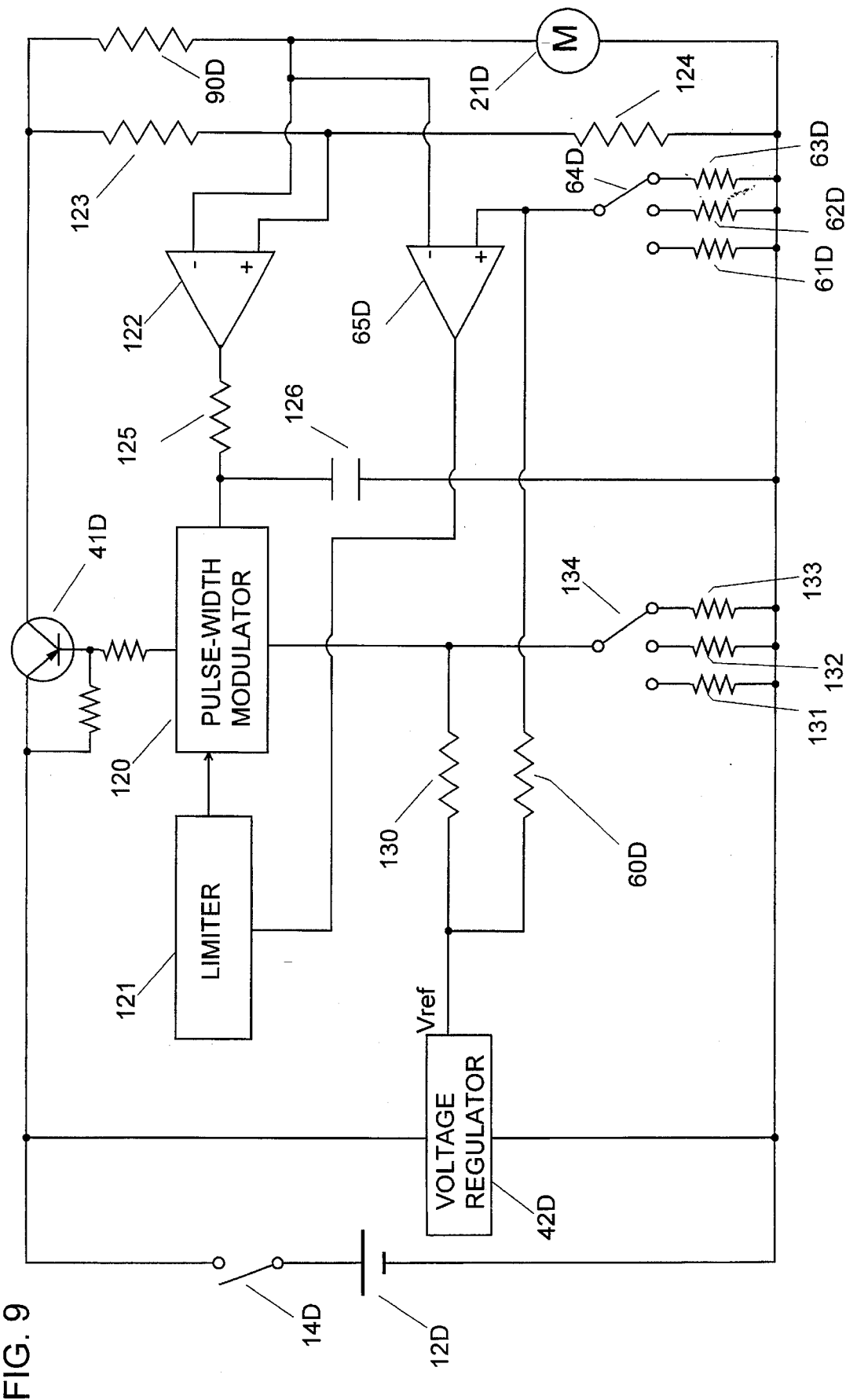
FIG. 9 is circuit diagram of an electric toothbrush in accordance with a fifth embodiment of the present invention.
Figure 10:
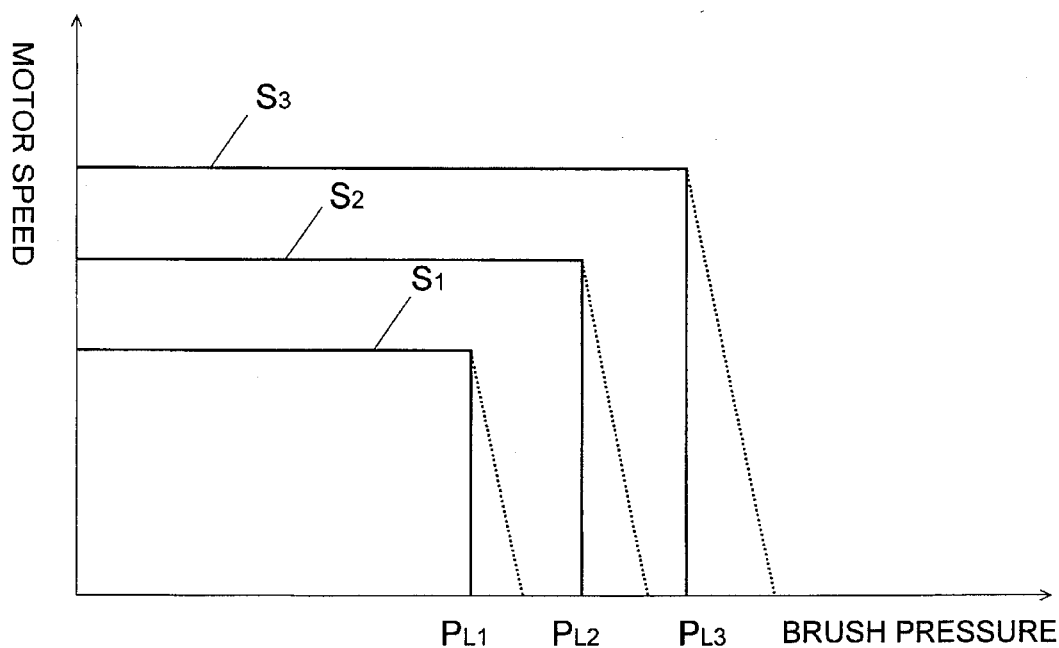
FIGS. 10 and 11 are graphs illustrating the operations of the circuit of FIG. 9.
Figure 11:
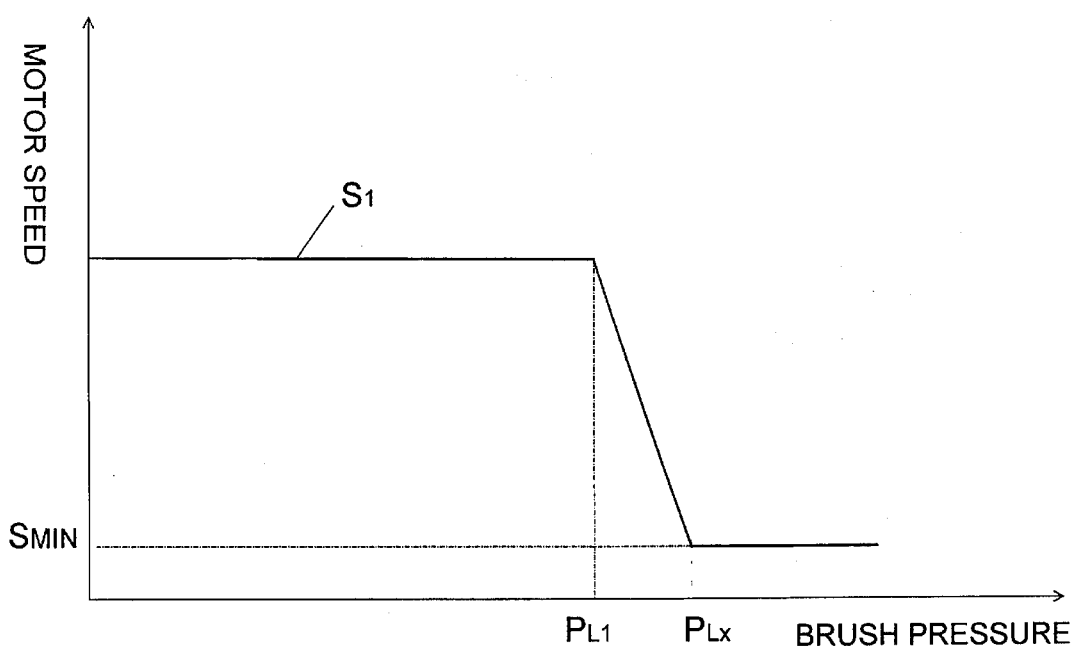

Fifth Embodiment <FIGS. 9 to 11>

FIG. 9 illustrates a circuit diagram of an electric toothbrush in accordance with a fifth embodiment of the present invention which is identical in mechanical structure to the first embodiment except that the brush pressure is measured in terms of a motor current flowing through the DC motor 21D. Like components are designated by like numerals with a suffix letter of "D". In this embodiment, transistor 41D connected in series with the motor 21D is controlled by a pulse-width modulator (PWM) 120 capable of varying a duty ratio of transistor 41D and therefore varying the rotation speed of the motor 21D. As will be discussed later, PWM 120 controls the transistor 41D to give a varying current to the motor when the motor speed tend to vary under the influence of the load, i.e., the brush pressure, in order to keep the motor 21D rotating at a constant speed selected by the user. In order to stop the motor 21D upon the brush pressure exceeding the limit level, the circuit includes a current sensing resistor 90D which is connected in series with the motor 21D to sense the motor current and provide a corresponding voltage to the non-inverting input of comparator 65D. Comparator 65D receives at its inverting input the limit voltage indicative of the limit pressure level at which the motor 21B stops. In a like manner as in the first embodiment, the limit voltage is selected from low, middle, and high voltages determined by dividing the reference voltage Vref from the voltage regulator 42D by the use of voltage dividers of common resistor 60D and first resistor 61D, of common resistor 60D and second resistor 62D, and of common resistor 60D and third resistor 63D. A switch 64D is provided to connect the common resistor 60D selectively to one of the resistors 61D to 63D of different resistivity to set the limit voltage of a particular level. Consequently, while the brush pressure is maintained below the limit level selected by the switch 64D, comparator 65D gives "H" output to a limiter 121 which responds to provide an enable signal to PWM 120 to keep rotating the motor at the selected speed. When the brush pressure exceeds the limit level with attendant high motor current flowing through resistor 90D, comparator 65D responds to provide "L" output to limiter 101, which in turn provides a disable signal to PWM 120 to thereby to turn off transistor 41D, thereby stop rotating the motor 21D. The motor 21D can resume rotating as the brush pressure lowers below the limit level. The limiter 121 may include a latch which hold the disable signal once the comparator 65D gives "H" output as indicative of the brush pressure exceeding the limit level so that the motor 21D is kept stalled even when the brush pressure lowers below the limit level and is only permitted to restart by switching off the power switch 14D followed by switching it on again.

PWM 120 is cooperative with a so-called bridge-servo or electronic governor to define a constant speed controller for rotating the motor 21D at a constant speed irrespective of variation in the brush pressure below the limit level. The speed controller relies upon a relation that the rotation speed is proportional to a reverse voltage developed at a winding of the motor. To this end, the speed controller comprises an operational amplifier 122 and a bridge composed of a series connected pair of resistors 123 and 124, and a series connected pair of current sensing resistor 90D and a resistance of the motor 21D. Operational amplifier 122 receives has its inverting and non-inverting inputs connected to the bridge so as to give an error voltage which is fed to PMW 120 to vary the duty ratio of transistor 41D in a direction of reducing the voltage difference between the bridge output. Therefore, when the motor speed is lowered from the selected speed as a result of increasing load or brush pressure, operational amplifier 122 provides a corresponding error voltage so that PWM 120 responds to increase the duty ratio of transistor 41D to give a large current to the motor 21D, thereby increasing the motor speed to the selected speed and therefore keep rotating the motor at the selected speed irrespective of variation in the brush pressure applied back to the motor to lower the rotation speed otherwise. A time constant circuit of resistor 125 and a capacitor 126 is connected to the output of operational amplifier 122 to determine a frequency at which PWM 120 controls the transistor 41D. PWM 120 includes a speed adjuster which controls to vary the duty ratio of transistor 41D in response to a speed voltage applied thereto. The speed voltage is determined by dividing the reference voltage Vref from the voltage regulator 42D by the use of voltage dividers of common resistor 130 and first resistor 131, of common resistor 130 and second resistor 132, and of common resistor 110 and third resistor 133. A switch 134 is provided to connect the common resistor 130 selectively to one of the resistors 131,132, 133 of different resistivity to set the speed voltage to a particular level. With the provision of the switches 64D and 134, it is made to select the limit level as well as the speed level respectively from set values to give more consistent control of tooth brushing depending upon differing user's requirements, as shown in FIG. 10, wherein PL1, PL2, PL3 denote the limit level selected by switch 64D, and S1, S2, S3 denote the motor speed selected by switch 134. In this connection, it should be noted that the limiter 121 may be configured to give such the disable signal which causes PWM to gradually decrease the duty ratio of transistor 41D to zero as the brush pressure further increases, thereby lowering the motor speed gradually to zero after the brush pressure exceeds the limit level, as shown in dotted lines in FIG. 10. Further, the limiter 121 may be alternately configured to give a limit signal instead of the disable signal for control of the motor speed, as shown in FIG. 11. That is, the limit signal is issued when the brush pressure exceeds the limit level PL1 and is fed to control PWM 120 to gradually decrease the duty ratio of transistor 41D and therefore the motor speed to a minimum level SMIN as the brush pressure further increases to another limit level PLX. In this modification, the limiter 121 is connected to constantly monitor the motor current to acknowledge the limit level PLX. Although not illustrated in this embodiment, the latch and reset switch as utilized in the embodiment of FIG. 6 are equally applicable to the present embodiment.

Figure 12:
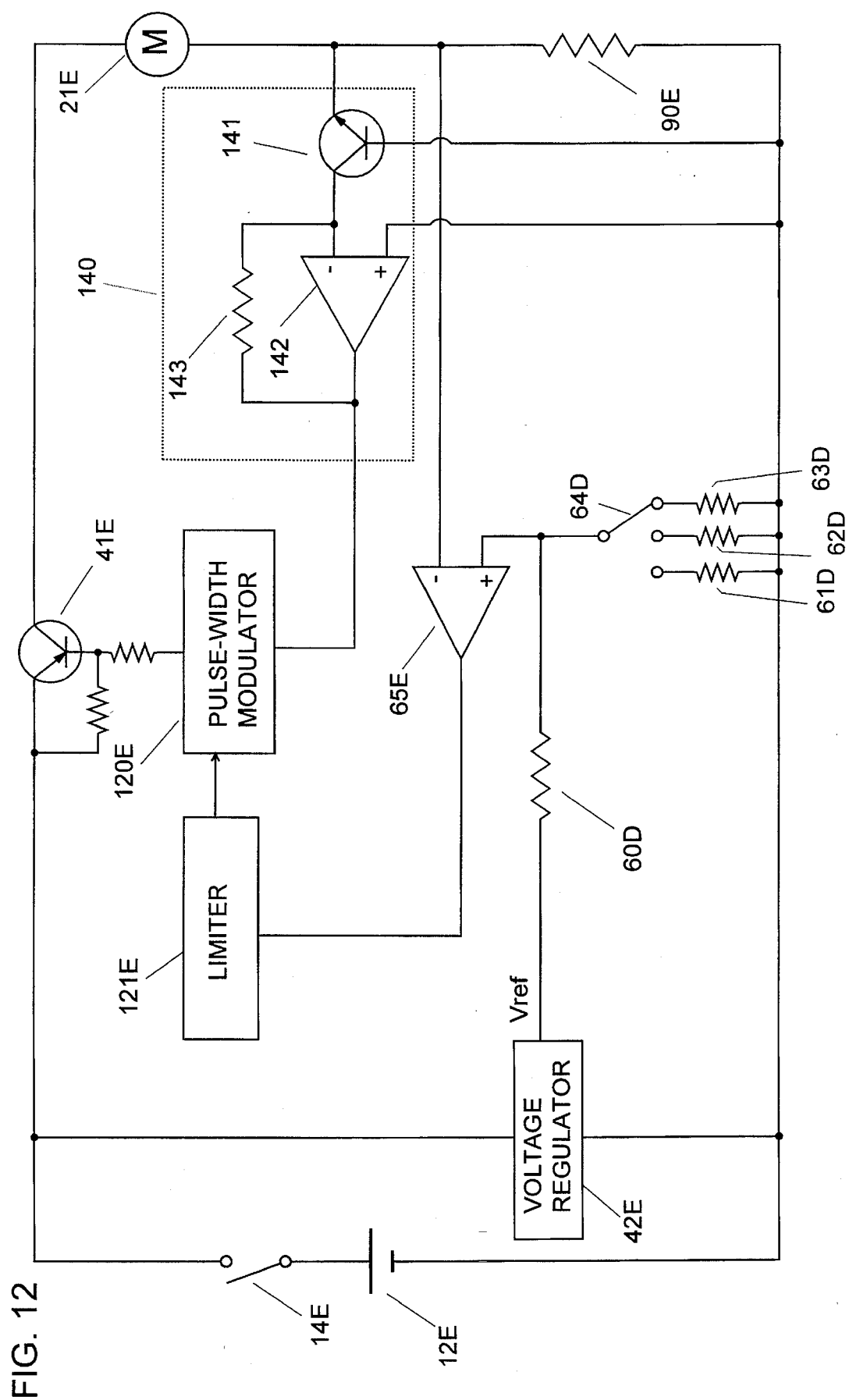
FIG. 12 is a circuit diagram of an electric toothbrush in accordance with a sixth embodiment of the present invention.

Sixth Embodiment <FIG. 12>

FIG. 12 illustrates a circuit diagram of an electric toothbrush in accordance with a sixth embodiment of the present invention which is similar to the embodiment of FIG. 9 except that PWM 120E is controlled to increase the motor speed as the brush pressure increases and stop the motor when the brush pressure exceed the limit level. Like components are designated by like numerals with a suffix letter of "E". Comparator 65E is connected to receive at its inverting input a voltage corresponding to the motor current flowing through resistor 90E as indicative of the brush pressure and receive at its non-inverting input the limit voltage selected by switch 64D from three set values determined by selective combination of resistors 60D to 63D. When the brush pressure is below the limit level given by the limit voltage, comparator 65E provide "H" output to limiter 121E which responds to give an enable signal to PWM 120E so that PWM 120E produces a drive pulse having a predetermined duty ratio to transistor 41E, thereby feeding a motor current to rotate the motor at a predetermined motor speed. When the brush pressure exceeds the limit level, comparator 65E produce "L" output to limiter 121E which responds to issue a disable signal to PWM 120E. Upon this occurrence, PWM 120E is disabled and stop feeding the drive pulse to transistor 41E, thereby stop the motor.

Figure 13:
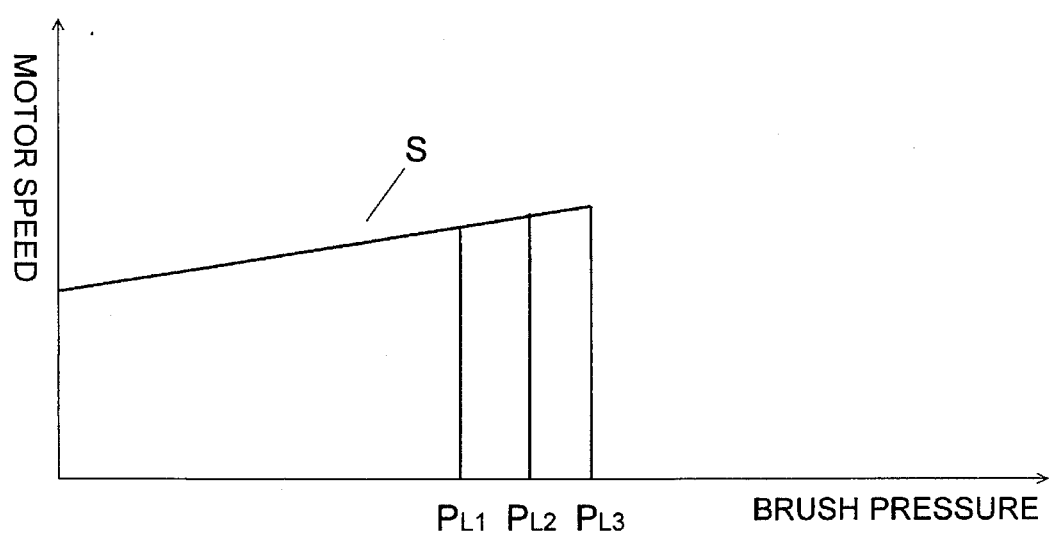
FIG. 13 is a graph illustrating the operation of the circuit of FIG. 12.

PWM 120E is connected to receive a control signal from an inverse logarithmic amplifier 140 so as to increase the duty ratio as the motor current increases for increasing the motor speed as the brush pressure increase within the limit level. The inverse logarithmic amplifier 140 comprises a transistor 141, an operational amplifier 142, and a feedback resistor 143 connected across the inverting input and output of amplifier 142. As the motor current increases as indicative that the brush pressure increases, the operational amplifier 142 provides a correspondingly increasing voltage as the control signal to PWM 120E which responds to increase the duty ratio of transistor 41E for flowing an increasing motor current, whereby increasing the motor speed S in proportion to the increasing brush pressure, as shown in FIG. 13. This proportional control, which is made until the brush pressure reaches the limit level PL1, PL2, and PL3 selected by the user, is most effective to perform the tooth brushing rapidly while avoiding to hurt the teeth and gums. Although not illustrated, the latch and reset switch as utilized in the embodiment of FIG. 6 are equally applicable to the present embodiment.

What is claimed is:

1. An electric toothbrush comprising:

a housing having a shaft mounting a brush, said housing incorporating a rotary electric motor and a motion converting mechanism which converts a rotational movement of said motor to a reciprocatory movement of said shaft for reciprocating said brush;

a pressure sensor which senses a brush pressure being applied back to said brush as a counter-pressure when pressing said brush against teeth of a user, and which provides a stop signal when said brush pressure exceeds a predetermined limit level; a selector to select a limit level from a plurality of set values; and a control circuit which is responsive to said stop signal for lowering the motor speed or stopping said motor.

2. An electric toothbrush as set forth in claim 1, wherein said pressure sensor provides said brush pressure which is a perpendicular component of said counter-pressure acting upon said brush in a direction perpendicular to a tip face of said brush.

3. An electric toothbrush as set forth in claim 1, wherein said control circuit is capable of restarting said motor in response to said brush pressure being lowered below said limit level.

4. An electric toothbrush as set forth in claim 1 wherein said control circuit includes constant speed means for rotating said motor at a constant level irrespective of variations in said brush pressure so long as said brush pressure is below said limit level.

5. An electric toothbrush as set forth in claim 1, wherein said pressure sensor is connected to said shaft, said pressure sensor provides an electric resistance which varies in proportion to said brush pressure applied back to said shaft and produces said stop signal when the electric resistance increases to a level corresponding to said limit level.

6. An electric toothbrush as set forth in claim 5, wherein said control circuit includes calibration means which obtains an initial current level measured when said motor rotates under substantially no load condition, and said calibration means defines said limit level as said initial current level plus a predetermined set level.

7. An electric toothbrush as set forth in claim 1, wherein said pressure sensor is in the form of a current sensor which monitors a motor current flowing through said motor as indicative of said brush pressure and produces said stop signal when said motor current exceeds a predetermined level corresponding to said limit level.

8. An electric toothbrush as set forth in claim 1, wherein said control circuit includes start means for starting said motor only after said brush pressure increases up to a predetermined start level which is lower than said limit level.

9. An electric toothbrush as set forth in claim 1, wherein said control circuit includes latch means which disables said motor to rotate once said brush pressure exceeds said limit level.

10. An electric toothbrush as set forth in claim 9, wherein said control circuit further includes reset means to release said latch means to enable said motor to restart when said brush pressure is below said limit level.

11. An electric toothbrush as set forth in claim 1, wherein said pressure sensor is a normally-closed switch which opens by application of pressure, said normally-closed switch being connected in series between said motor and battery and caused to open in response to said brush pressure exceeding said limit level, thereby stopping said motor.

12. An electric toothbrush as set forth in claim 11, further including a normally-open start switch which closes by application of pressure, said start switch being connected in series with said normally-closed switch and caused to close in response to said brush pressure reaching a predetermined starting pressure level.

13. An electric toothbrush comprising:

a housing having a shaft mounting a brush, said housing incorporating a rotary electric motor and a motion converting mechanism which converts a rotational movement of said motor to a reciprocatory movement of said shaft for reciprocating said brush;

a pressure sensor which senses a brush pressure being applied back to said brush as a counter-pressure when pressing said brush against teeth of a user, and which provides a stop signal when said brush pressure exceeds a predetermined limit level; and a control circuit which is responsive to said stop signal for lowering the motor speed or stopping said motor, said control circuit including a constant speed means for rotating said motor at a constant level irrespective of variations in said brush pressure so long as said brush pressure is below said limit level and a speed selector for selecting the constant speed rotation speed of said motor.

14. An electric toothbrush as set forth in claim 13, wherein said constant speed means rotates said motor at said constant level until said brush pressure reaches said limit level, and lowers said motor speed as said brush pressure increases beyond said limit level.

15. An electric toothbrush comprising:

a housing having a shaft mounting a brush, said housing incorporating a rotary electric motor and a motion converting mechanism which converts a rotational movement of said motor to a reciprocatory movement of said shaft for reciprocating said brush;

a pressure sensor which senses a brush pressure being applied back to said brush as a counter-pressure when pressing said brush against teeth of a user, and which provides a stop signal when said brush pressure exceeds a predetermined limit level; and a control circuit which is responsive to said stop signal for lowering the motor speed or stopping said motor, said control circuit including constant speed means for rotating said motor at a constant level irrespective of variations in said brush pressure so long as said brush pressure is below said limit level, said control circuit providing a first limit mode and a second limit mode selectively, said first limit mode enabling said motor to rotate at a first constant rotation speed irrespective of said brush pressure so long as said brush pressure is below a first limit level, said second limit mode enabling said motor to rotate at a second constant rotation speed irrespective of said brush pressure so long as said brush pressure is below a second limit level, said first rotation speed and said first limit level being respectively lower than said second rotation speed and said second limit level.

16. An electric toothbrush comprising:

a housing having a shaft mounting a brush, said housing incorporating a rotary electric motor and a motion converting mechanism which converts a rotational movement of said motor to a reciprocatory movement of said shaft for reciprocating said brush;

a pressure sensor which senses a brush pressure being applied back to said brush as a counter-pressure when pressing said brush against teeth of a user, and which provides a stop signal when said brush pressure exceeds a predetermined limit level; and a control circuit which is responsive to said stop signal for lowering the motor speed or stopping said motor, said control circuit including proportional means for increasing the rotational speed of said motor in proportion to an increase in said brush pressure so long as said brush pressure is below said limit level.

17. An electric toothbrush comprising:

a housing having a shaft mounting a brush, said housing incorporating a rotary electric motor and a motion converting mechanism which converts a rotational movement of said motor to a reciprocatory movement of said shaft for reciprocating said brush;

a pressure sensor which senses a brush pressure being applied back to said brush as a counter-pressure when pressing said brush against teeth of a user, and which provides a stop signal when said brush pressure exceeds a predetermined limit level;

said pressure sensor comprising means which monitors a waveform of a motor current flowing through said motor and analyzes said waveform for deriving said brush pressure, said monitor means producing said stop signal when said brush pressure exceeds said limit level; and a control circuit which is responsive to said stop signal for lowering the motor speed or stopping said motor.

18. An electric toothbrush comprising:

a housing having a shaft mounting a brush, said housing incorporating a rotary electric motor and a motion converting mechanism which converts a rotational movement of said motor to a reciprocatory movement of said shaft for reciprocating said brush;

a pressure sensor connected to said shaft and which senses a brush pressure being applied back to said brush as a counter-pressure when pressing said brush against teeth of a user, and which provides an electric resistance which varies in proportion to said brush pressure applied back to said shaft and produces a stop signal when the electric resistance increases to a level corresponding to a predetermined limit level; and a control circuit which is responsive to said stop signal for lowering the motor speed or stopping said motor, said control circuit including calibration means which obtains an initial current level measured when said motor rotates under substantially no load condition, and said calibration means defining said limit level as said initial current level plus a predetermined set level.

19. An electric toothbrush as set forth in claim 18, wherein said control circuit is capable of restarting said motor in response to said brush pressure being lowered below said limit level.

20. An electric toothbrush as set forth in claim 18, wherein said control circuit includes constant speed means for rotating said motor at a constant level irrespective of variations in said brush pressure so long as said brush pressure is below said limit level.

21. An electric toothbrush as set forth in claim 20, wherein said constant speed means rotates said motor at said constant level until said brush pressure reaches said limit level, and lowers said motor speed as said brush pressure increases beyond said limit level.

22. An electric toothbrush as set forth in claim 18, wherein said control circuit includes start means for starting said motor only after said brush pressure increases up to a predetermined start level which is lower than said limit level.

23. An electric toothbrush as set forth in claim 18, wherein said control circuit includes latch means which disables said motor to rotate once said brush pressure exceeds said limit level.

* * * * *